United States Patent [19]

Schiehser et al.

[11] Patent Number: 5,053,508
[45] Date of Patent: Oct. 1, 1991

[54] FUSED HETEROTRICYCLIC IMIDES WITH PSYCHOTROPIC ACTIVITY AND INTERMEDRATES THEREOF

[75] Inventors: Guy A. Schiehser, Yardley; Magid A. Abou-Gharbia, Glen Mills, both of Pa.; Charles Lin, Plattsburgh, N.Y.

[73] Assignee: American Home Products Corporation, New York, N.Y.

[21] Appl. No.: 491,143

[22] Filed: Mar. 9, 1990

[51] Int. Cl.$^5$ .................................... C07D 498/02
[52] U.S. Cl. .................... 544/357; 544/238; 544/295; 544/360; 544/368; 548/242; 548/430
[58] Field of Search ............... 544/295, 357, 238, 360; 548/242

[56] References Cited

U.S. PATENT DOCUMENTS

| | | | |
|---|---|---|---|
| 4,479,954 | 10/1984 | Hirose | 544/360 |
| 4,732,984 | 3/1988 | Abou-Gharbia et al. | 544/295 |
| 4,748,240 | 5/1988 | Stack et al. | 544/357 |
| 4,748,247 | 5/1988 | Abou-Gharbia | 544/357 |
| 4,797,488 | 1/1989 | Stack et al. | 544/295 |
| 4,843,078 | 6/1989 | Ishizomi et al. | 544/295 |
| 4,855,430 | 8/1989 | Abou-Gharbia et al. | 544/295 |
| 4,892,943 | 1/1990 | Abou-Gharbia | 544/295 |
| 4,927,934 | 5/1990 | Abou-Gharbia et al. | 544/295 |
| 4,957,913 | 9/1990 | Abou-Gharbia et al. | 514/253 |

OTHER PUBLICATIONS

Abou-Gharbia et al. *J. Med. Chem.*, 1988, 31, 1382–1392.

Primary Examiner—Donald G. Daus
Attorney, Agent, or Firm—George Tarnowski

[57] ABSTRACT

There are disclosed compounds of the formula

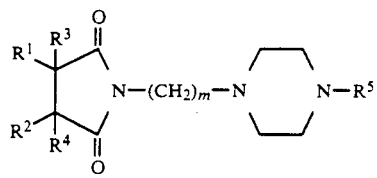

wherein
R$^1$ and R$^2$ taken together represent

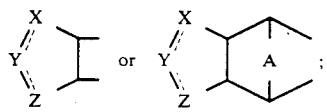

R$^3$ and R$^4$ are hydrogen;
R$^5$ is 2-pyridinyl, 2-pyrazinyl, 2-pyrimidinyl, 3-pyridazinyl or any of the foregoing R$^5$ moieties substituted by lower alkyl, lower alkoxy, halo lower alkyl, cyano, nitro or halo;
X, Y and Z are, independently, N, S, O, NR$^6$, SO, SO$_2$, CR$^6$ or CH$_2$;
A is lower alkylene, O or S;
R$^6$ is hydrogen, lower alkyl, aryl, aralkyl;
m is 3–7;

and the pharmaceutically acceptable salts thereof, and their use as antipsychotic/-anxiolytic agents having a low liability for extrapyramidal side effects.

8 Claims, No Drawings

FUSED HETEROTRICYCLIC IMIDES WITH PSYCHOTROPIC ACTIVITY AND INTERMEDRATES THEREOF

This invention relates to novel compounds having antipsychotic activity and being characterized by the general formula

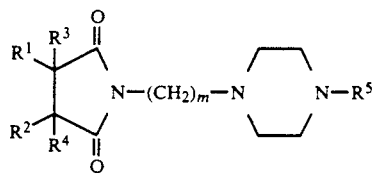

wherein
R¹ and R² taken together represent

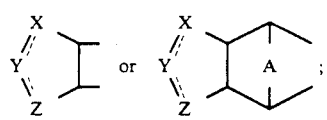

R³ and R⁴ are hydrogen;
R⁵ is 2-pyridinyl, 2-pyrazinyl, 2-pyrimidinyl, 3-pyridazinyl or any of the foregoing R⁵ moieties substituted by lower alkyl, lower alkoxy, halo lower alkyl, cyano, nitro or halo;
X, Y and Z are, independently, N, S, O, NR⁶, SO, SO₂, CR⁶ or CH₂;
R⁶ is hydrogen, lower alkyl, aryl, aralkyl;
A is lower alkylene, O or S;
m is 3-7;
and the pharmaceutically acceptable salts thereof.

The terms "lower alkyl" and "lower alkoxy" refer to moieties having 1-4 carbon atoms in the carbon chain. The term "aryl" refers to moieties having 6-10 carbon atoms while "aralkyl" refers to aryl moieties having 1-6 carbon atoms in the alkyl carbon chain. The term "halo" refers to fluoro, chloro and bromo.

The five-membered heterocyclic rings fused to the succinimide moiety via a cyclobutyl or 1,6-bridged cyclohexyl ring and defined by the substituents X, Y and Z embrace but are not limited to such groups as cyclopentane, furan, thiophene, pyrrole, isopyrrole, pyrazole, 2-isoimidazole, imidazole, 1,2,3-triazole, dithiole, oxathiazole, isoxazole, oxazole, thiazole, isothiazole, oxadiazole, dioxazole, oxathiole, furazan, the mono- and dioxides of the sulfur containing heterocycles, and the like.

The compounds of the invention can form pharmacologically acceptable salts from pharmacologically acceptable organic and inorganic acids such as hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. For example, sulfolene can be irradiated in the presence of maleimide to yield an adduct which, when reacted with a suitable dihaloalkane affords an intermediate product:

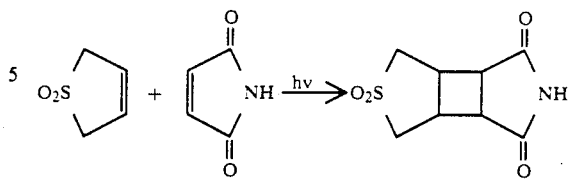

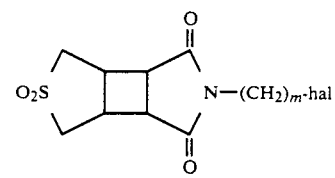

The intermediate product can then be reacted with an appropriately substituted 4-piperazine to yield the desired final product

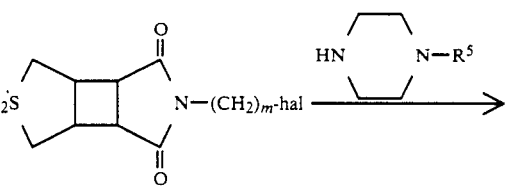

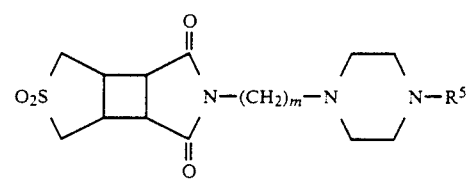

In a similar manner, cyclopentene can be irradiated with maleic anhydride to afford an intermediate:

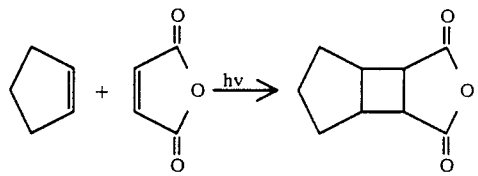

The intermediate can then be reacted with a suitable 1-substituted piperazine-4-alkylamine to yield the desired final product

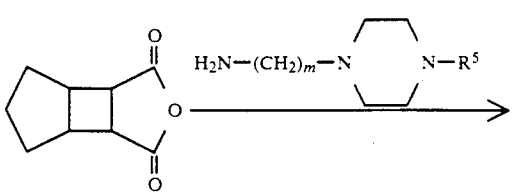

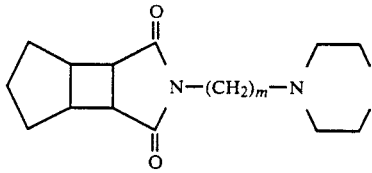

Compounds of the invention in which $R^1/R^2$ represent the moiety

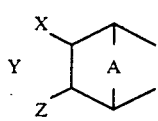

can be prepared by a 1,3-dipolar cycloaddition of a suitable precursor to an unsaturated bicyclic derivative. Thus, for example, methyl nitrile oxide can be cycloadded to norbornene dicarboxylic acid anhydride as follows:

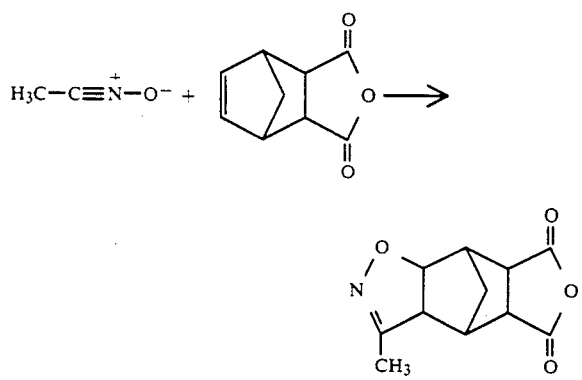

The resulting intermediate can then be reacted according to the above outlined reaction scheme to obtain the desired final product:

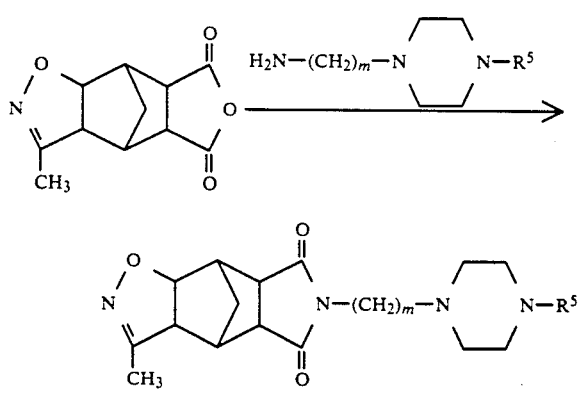

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses, the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

5-[4-[4-(6-chloro-2-pyrazinyl)-1-piperazinyl]butyl]tetrahydro-1H-thieno[3',4':3,4]cyclobuta[1,2-c]pyrrole-4,6(3H,5H)-dione 2,2 dioxide hydrochloride

A.

Tetrahydro-1H-thieno[3',4':3,4]cyclobuta[1,2-c]pyrrole-4,6(3H,5H)-dione 2,2-dioxide A solution of 5.0 g (0.42 mol) of sulfolene and 4.1 g (0.42 mol) of maleimide in 40 ml of dry acetone in a quartz tube is sealed with a rubber septum stopper and degassed with nitrogen. The solution is then irradiated with quartz-filtered light while cooling in ice for 3 hours. The separated white precipitate is filtered, washed with ethyl acetate and dried to afford 2.0 g of the desired sulfolene-maleimide photoadduct: m.p. 320°–322° C. (decomp) which is used without further purification to prepare the title compound.

B.

5-(4-bromobutyl)tetrahydro-1H-thieno[3',4':3,4]cyclobuta[1,2-c]pyrroli4,6(3H,5H)dione 2,2-dioxide The sulfolene-maleimide adduct (2.0 g, 9 mmol) is dissolved in 40 ml of DMF. To the stirred solution, 0.3 g of sodium hydride is added and stirring is continued for 1 hour. The resulting solution is added dropwise to a solution of 4.0 g (0.01 mol) of 1,4-dibromobutane in 40 ml of dimethylformamide. The mixture is maintained while stirring at room temperature for 20 hours. The solvent is evaporated under high vacuum and the residue partitioned between methylene chloride and water. The methylene chloride extracts are combined, washed with water and dried over anhydrous sodium sulfate. Filtration and removal of the solvent in vacuo gives the title compound as on oily solid which is used without further purification.

C.

5-[4-[4-(6-chloro-2-pyrazinyl)-1-piperazinyl]butyl]tetrahydro-1H-thieno[3',4':3,4]cyclobuta[1,2-c]pyrrole-4,6(3H,5H)-dione 2,2 dioxide, hydrochloride A solution of 2.0 g of 5-(4-bromobutyl)tetrahydro-1H-thieno-[3',4':3,4]cyclobuta[1,2-c]pyrrole-4,6(3H,5H)dione 2,2-dioxide in 50 ml of dimethylformamide is added to a stirred solution 2.0 g (0.007 mol) of 1-(6-chloro-2-pyrazinyl)-piperazine hydrochloride and 4 ml of triethylamine. The reaction mixture is stirred overnight and the solvent is removed under vacuum. The residue is partitioned between water and methlene chloride. The methylene chloride extracts are combined, washed with brine and dried over anhydrous sodium sulfate. Filtration and roto-evaporation gives the crude free base. Preparative HPLC [silica gel; ethyl acetate:methylene chloride (9:1)] followed by evaporation of the appropriate fractions (TLC Rf=0.4), treatment with ethanolic hydrogen chloride and recrystallization from ethanol gives the title compound: m.p. 154°–157° C.

Analysis for: $C_{20}H_{26}ClN_5SO_4 \cdot HCl$. Calculated: C, 47.61; H, 5.35; N, 13.88. Found: C, 48.43; H, 4.84; N, 14.61.

EXAMPLE 2

5-[4-[4-(3-chloro-2-pyrazinyl)-1-piperazinyl]butyl]tetrahydro-1H-thieno[3',4':3,4]cyclobuta[1,2-c]pyrrole-4,6(3H,5H)dione 2,2-dioxide, hydrochloride The title compound is prepared following the procedure of Example 1 with the exception that 1-(3-chloro-2-pyrazinyl)piperazine hydrochloride is used instead of 1-(6-chloropyrazinyl)piperazine hydrochloride affording the hydrochloride salt: m.p. 238°–240° C.

Analysis for: $C_{20}H_{26}ClN_5SO_4 \cdot HCl$. Calculated: C, 47.61; H, 5.35; N, 13.88. Found: C, 47.20; H, 5.51; N, 13.38.

EXAMPLE 3

(3a,3b,6a,6b)-tetrahydro-5-[4-[4-(2-pyrimidinyl)-1-piperazinyl]butyl]-1H-thieno[3',4':3,4]cyclobuta[1,2-c]pyrrole-4,6(3H,5H)-dione 2,2-dioxide, dihydrobromide, hemihydrate The title compound is prepared following the procedure of Example 1 with the exception that 1-(2-pyrimidinyl)piperazine hydrochloride is used instead of 1-(6-chloropyrazinyl)piperazine hydrochloride and the hydrobromide salt is prepared instead of the hydrochloride salt: m.p. 262°–264° C.

Analysis for: $C_{20}H_{27}SN_5O_4 \cdot 2HBr \cdot 0.5H_2O$. Calculated: C, 39.73; H, 4.96; N, 11.58. Found: C, 39.67; H, 4.73; N, 11.03.

EXAMPLE 4

Hexahydro-1H-cyclopenta[3,4-c]cyclobuta[1,2-c]furan-1,3(3aH)-dione

A solution of cyclopentene (20.0 g, 0.305 mol), maleic anhydride (20.0 g, 0.204 mol) in 250 ml of methylene chloride in a 500 ml Vycor photochemical cell is degassed with nitrogen. The solution is irradiated with a quartz-filtered light while cooling in an ice bath for 3.5 hours. TLC indicates complete reaction (absence of maleic anhydride). The solution is evaporated to dryness to afford a gummy residue which is dissolved in ethyl acetate (300 ml). Upon addition of ethyl ether, a white precipitate is formed which is filtered and dried under vacuum to give the title compound: m.p.>350° C. NMR and IR spectra are consistent with the expected photoadduct and the product is used without further purification.

The title compound is prepared by refluxing 2.0 g (0.012 mol) of the cyclopentene-maleic anhydride photoadduct with 3.5 g (0.01 mol) of 1-(4-aminobutyl)-4-(2-pyrimidinyl)piperazine in 50 ml of dry pyridine overnight. The solvent is removed under reduced pressure and the remaining oil is purified by HPLC using ethyl acetate as an eluent. The title compound is converted to the hydrochloride salt by dissolving in ethanol and adding 2 ml of ethanol-saturated with hydrogen chloride: m.p. 178°–179° C.

Analysis for: $C_{21}H_{27}N_5O_2 \cdot 2HCl \cdot \frac{1}{2}H_2O$. Calculated: C, 54.42; H, 6.47; N, 15.11. Found: C, 54.89; H, 6.91; N, 15.67.

EXAMPLE 5

3a,4,4a,7a,8,8a-hexahydro-3-methyl-4,8-methanofuro[3,4-f]-1,2-benzisoxazole-5,7-dione A solution of 4.0 g (24.4 mmol) of cis-5-norbornene-endo-2,3-dicarboxylic anhydride and 5.8 g (48.8 g) of phenyl isocyanate in 20 ml of tetrahydrofuran is treated dropwise with a solution of 1.83 g (1.76 ml, 24.4 mmol) of nitroethane and 6 drops of triethylamine in 10 ml of tetrahydrofuran. The mixture is maintained with stirring for 1 hour. The reaction mixture is filtered and the filtrate evaporated. Trituration with ethyl ether, filtration and drying gives 3.97 g of crude product. Trituration with 100 ml of ethanol (2 times) gives after filtration and drying 2.28 g of the title compound: m.p. 194°–197° C.

Analysis for: $C_{11}H_{11}NO_4$. Calculated: C, 59.72; H, 5.01; N, 6.33. Found: C, 59.55; H, 5.06, N, 6.31.

EXAMPLE 6

6-[4-[4-(6-chloro-2-pyrazinyl)-1-piperazinyl]butyl]-3a,4,4a,7a,8,8a-hexahydro-3-methyl-4,8-methano-5H-pyrrolo[3,4-f]-1,2-benzisoxazole-5,7(6H)-dione, ethanedioate (1:1)

A mixture of 995 mg (4.5 mmol) of 3a,4,4a,7a,8,8a-hexahydro-3-methyl-4,8-methanofuro[3,4-f]-1,2-benzisoxazole-5,7-dione and 1.35 g (5 mmol) of 4-[4-(6-chloro-2-pyrazinyl)-1-piperazinyl]butylamine in 25 ml of pyridine is heated to reflux under nitrogen (bath temperature 140 C) for 17.25 hours. The reaction mixture is rotoevaporated and the resulting residue is subjected to preparative HPLC. The appropriate fractions are combined, evaporated, dissolved in absolute ethanol and treated with a solution of 450 mg (5 mmol) of oxalic acid in absolute ethanol. Filtration of the obtained crystalline material gives a filtrate which is evaporated and partitioned between aqueous sodium bicarbonate and methylene chloride. The organic phase is dried over magnesium sulfate, filtered and evaporated to give 1.87 g (4.3 mmol) of an oil. The oil is dissolved in absolute ethanol and treated with a solution of 384 mg (4.3 mmol) of oxalic acid in ethanol. The obtained crystalline product is filtered and dried to afford 1.51 g of the title compound: m.p. 228°–230° C.

Analysis for: $C_{23}H_{29}ClN_6O_3 \cdot C_2H_2O_4$. Calculated: C, 53.33; H, 5.55; N, 14.93. Found: C, 53.28; H, 5.62; N, 14.56.

EXAMPLE 7

6-[4-[4-(2-pyrazinyl)-1-piperazinyl]butyl]-3a,4,4a,7a,8,8a-hexahydro-3-methyl-4,8-methano-5H-pyrrolo[3,4-f]-1,2-benzisoxazole-5,7(6H)-dione, ethanedioate (1:1), hemiethanolate A mixture of 995 mg (4.5 mmol) of 3a,4,4a,7a,8,8a-hexahydro-3-methyl-4,8-methanofuro[3,4-f]-1,2-benzisoxazole-5,7-dione and 1.2 g (5 mmol) of 4-[4-(2-pyrazinyl)-1-piperazinyl]butylamine in 25 ml of pyridine is heated to reflux under a nitrogen atmosphere and is maintained with stirring for 24 hours. The reaction mixture is partitioned between methylene chloride and water and the organic layer is washed with brine and dried over magnesium sulfate. Filtration and evaporation gives crude product which is chromatographed sequentially on silica gel using methylene chloride:methanol (9:1) and then ethyl acetate:methanol (9:1) as eluting solvents. The free base of the title compound is treated with ethanolic oxalic acid to give 490 mg of the title compound: m.p. 175°–178° C.

Analysis for: $C_{23}H_{30}N_6O_3 \cdot C_2H_2O_4 \cdot 0.5EtOH$. Calculated: C, 56.51; H, 6.40; N, 15.24. Found: C, 56.09, H, 5.98; N, 15.44.

EXAMPLE 8

6-[4-[4-2-pyrimidinyl)-1-piperazinyl]butyl]-3a,4,4a,7a,8,8a-hexahydro-3-methyl-4,8-methano-5H-pyrrolo[3,4-f]-1,2-benzisoxazole-5,7(6H)-dione, dihydrochloride, hydrate A mixture of 900 mg (4.1 mmol) of 3a,4,4a,7a,8,8a-hexahydro-3-methyl-4,8-methanofuro[3,4-f]-1,2-benzisoxazole-5,7-dione and 1.5 g (6.4 mmol) of 4-[4-(2-pyrimidinyl)-1-piperazinyl]butylamine in 25 ml of pyridine is heated to reflux and is maintained for 16.5 hours. The mixture is diluted with water and methylene chloride and is extracted with methylene chloride. The combined organic extracts are combined, dried over magnesium sulfate and evaporated. Column chromatography on silica gel using methylene chloride:methanol (9:1) gives the free base of the title compound. The compound is treated with excess ethanolic hydrochloric acid, rotoevaporated and dissolved in absolute ethanol. The solution is diluted with acetonitrile and rotoevaporated to give 454 mg of the title compound as a foam: m.p. 140°–150° C.

Analysis for: $C_{24}H_{32}N_6O_3 \cdot C_2H_2O_4$. Calculated: C, 57.55; H, 6.32; N, 15.49. Found: C, 57.50; H, 6.22; N, 15.14.

EXAMPLE 9

3a,4,4a,7a,8,8a-hexahydro-3-methyl-4,8-ethanofuro[3,4-f]-1,2-benzisoxazol-5,7-dione To a solution of 10.0 g (56.1 mmol) of endo-bicyclo[2.2.2]-oct-5-ene-2,3-dicarboxylic acid anhydride and 12.2 ml (112 mmol) of phenyl isocyanate in 50 ml of sieve-dried tetrahydrofuran under a nitrogen atmosphere is added dropwise a solution of 4.0 ml (56.0 mmol) of nitroethane and 0.5 ml of triethylamine in tetrahydrofuran. Precipitation is noted after 1.25 hours and stirring is maintained for an additional 3 hours. Filtration affords 6.9 g of crude product which is used without further purification.

EXAMPLE 10

6-[4-[4-(2-pyrimidinyl)-1-piperazinyl]butyl]-3a,4,4a,7a,8,8a-hexahydro-3-methyl-4,8-ethano-5H-pyrrolo[3,4-f]-1,2-benzisoxazole-5,7(6H)-dione, ethanedioate (1:1)

To a solution of 1.2 g (5.4 mmol) of 3a,4,4a,7a,8,8a-hexahydro-3-methyl-4,8-ethanofuro[3,4-f]-1,2-benzisoxazol-5,7-dione is added a solution of 1-(4-aminobutyl)-4-(2-pyridinyl)piperazine in 15 ml of pyridine. The mixture is heated to reflux for 3 hours and is allowed to stand overnight. The reaction mixture is diluted with water and partitioned with methylene chloride. The combined methlene chloride extracts are dried over magnesium sulfate, filtered, and evaporated. Preparative column chromatography on silica gel using ethyl acetate:methanol (95:5 through 85:15) affords 1.0 g of free base which is converted to 700 mg of the oxalate salt of the title compound: m.p. 150°–154° C. to give a second solid m.p. 165°–169° C.

Analysis for: $C_{24}H_{32}N_6O_3 \cdot C_2H_2O_4$. Calculated: C, 57.55; H, 6.32; N, 15.49. Found: C, 56.77; H, 6.21; N, 15.03.

EXAMPLE 11

6-[4-[4-(2-pyrazinyl)-1-piperazinyl]butyl]-3a,4,4a,7a,8,8a-hexahydro-3-methyl-4,8-ethano-5H-pyrrolo[3,4-f]-1,2-benzisoxazole-5,7(6H)-dione, ethanedioate (1:1)

To a solution of 1.5 g (6.8 mmol) of 3a,4,4a,7a,8,8a-hexahydro-3-methyl-4,8-ethanofuro[3,4-f]-1,2-benzisoxazol-5,7-dione in 100 ml of pyridine is added 2.80 g (12.0 mmol) of 1-(4-aminobutyl)-4-(2-pyrazinyl)piperazine and the mixture is heated to reflux and maintained overnight. The mixture is diluted with water and extracted with methylene chloride. The combined methylene chloride extracts are washed with brine, dried over magnesium sulfate and evaporated. The residue is subjected to HPLC to give 632 mg of crude product. Treatment with oxalic acid in ethanol gives after drying 516 mg of the title compound: m.p. 188°–202° C.

Analysis for: $C_{24}H_{32}N_6O_3 \cdot C_2H_2O_4$. Calculated: C, 57.55; H, 6.32; N, 15.49. Found: C, 57.50; H, 6.22; N, 15.14.

EXAMPLE 12

The compounds of the invention are tested in an assay to determine their ability to antagonize apomorphine-induced stereotyped behavior. The assay measures the in vivo dopamine receptor blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80 ® in water, are administered at several dose levels to male mice (6/dose level). A control group, run simultaneously with drug groups, receives equal volumes of solvent. Thirty minutes later (i.p. administration), drug-treated and control mice are challenged with 10 mg/kg apomorphine s.c. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| Standard Compounds: | $ED_{50}$ and 95% confidence interval, mg/kg intraperitoneal |
|---|---|
| Haloperidol | 1.37 (0.88–2.34) |
| Chloropromazine | 8.48 (4.79–16.38) |
| Clozapine | 30.06 (19.42–48.21) |

The compounds of the invention and buspirone, when tested in this assay are inactive, evidencing a low potential for exhibiting extrapyramidal side effects, such as pseudoparkinsonism, tardive dyskinesia and the like.

EXAMPLE 13

A test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber (10½"×6¾"×11⅞" high) and an elevated chamber or shelf (5⅝"×6⅝"×5¾"). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance responding and the dose calculated to produce a 50% block in avoidance responding ($AB_{50}$) is obtained from a dose-effect regression line fitted by the method of least squares. Potential antipsychotic compounds suppress avoidance responding and increase escape responding.

| Standard Compounds: | $AB_{50}$ (mg/kg i.p.) |
|---|---|
| Haloperidol | 0.19 |
| Chlorpromazine | 3.69 |
| Clozapine | 6.94 |
| Buspirone | 9.44 |

The results for compounds of this invention in this test are presented in Table I.

TABLE I

| Compound of Example No. | Active at mg/kg |
|---|---|
| 1 | 40 (i.p. and p.o.)* |
| 2 | 40 (i.p.) |
| 6 | 40 (i.p.) |
| 7 | 40 (i.p.) |
| 8 | 40 (i.p.) |
| 10 | 40 (i.p.) |
| 11 | 40 (i.p.) |

*(i.p.) = intraperitoneally administered drug
(p.o.) = perorally administered drug The results show that compounds of the invention are active intraperitoneally in this test.

What is claimed is:

1. A compound having the formula

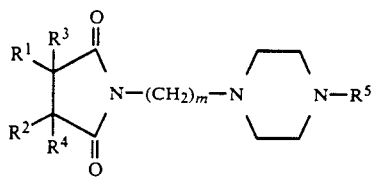

wherein
R$^1$ and R$^2$ taken together represent

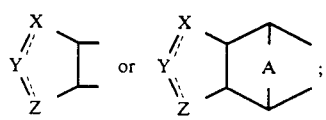

R$^3$ and R$^4$ are hydrogen;
R$^5$ is 2-pyridinyl, 2-pyrazinyl, 2-pyrimidinyl, 3-pyridazinyl or any of the foregoing R$^5$ moieties substituted by lower alkyl of 1-6 carbon atoms, lower alkoxy of 1-6 carbon atoms, halo lower alkyl of 1-6 carbon atoms, cyano, nitro or halo;
X, Y and Z are, independently, N, S, O, NR$^6$, CR$^6$ or CH$_2$, such that X, Y, and Z form a partially saturated or unsaturated 5-membered heterocycle selected from pyrrole, isopyrrole, pyrazole, 1,2,3-triazole, 1,3-dithiole, 1,2,3-oxathiole, isoxazole, or isothiazole; with the proviso that if X, Y, or Z is CR$^6$, one of the adjacent positions is CR$^6$ or N and if X, Y, or Z is N, one of the adjacent positions is N or CR$^6$;
A is lower alkylene of 1-4 carbon atoms, O or S;
R$^6$ is hydrogen, lower alkyl of 1-6 carbon atoms, aryl of 6-10 carbon atoms, aralkyl having 1-6 carbons in the alkyl chain;
m is 3-7;
and the pharmaceutically acceptable salts thereof.

2. A compound having the name 3a,4,4a,7a,8,8a-hexahydro-3-methyl-4,8-methanofuro[3,4-f]-1,2-benzisoxazole-5,7-dione.

3. The compound of claim 1, having the name 6-[4-[4-(6-chloro-2-pyrazinyl)-1-piperazinyl]butyl]-3a,4,,4a,7a,8,8a-hexahydro-3-methyl-4,8-methano-5H-pyrrolo[3,4-f]-1,2-benzisoxazole-5,7(6H)-dione.

4. The compound of claim 1, having the name 6-[4-[4-(2-pyrazinyl)-1-piperazinyl]butyl]-3a,4,4a,7a,8,8a-hexahydro-3-methyl-4,8-methano-5H-pyrrolo[3,4-f]-1,2-benzisoxazole-5,7(6H)-dione.

5. The compound of claim 1, having the name 6-[4-[4-2-pyrimidinyl)-1-piperazinyl]butyl]-3a,4,4a,7a,8,8a-hexahydro-3-methyl-4,8-methano-5H-pyrrolo[3,4-f]-1,2-benzisoxazole-5,7(6H)-dione.

6. A compound having the name 3a,4,4a,7a,8,8a-hexahydro-3-methyl-4,8-ethanofuro[3,4-f]-1,2-benzisoxazol-5,7-dione.

7. The compound of claim 1, having the name 6-[4-[4-(2-pyrimidinyl)-1-piperazinyl]butyl]-3a,4,4a,7a,8,8a-hexahydro-3-methyl-4,8-ethano-5H-pyrrolo[3,4-f]-1,2-benzisoxazole-5,7(6H)-dione.

8. The compound of claim 1, having the name 6-[4-[4-(2-pyrazinyl)-1-piperazinyl]butyl]-3a,4,4a,7a,8,8a-hexahydro-3-methyl-4,8-ethano-5H-pyrrolo[3,4-f]-1,2-benzisoxazole-5,7(6H)-dione.

* * * * *